Figure 1:
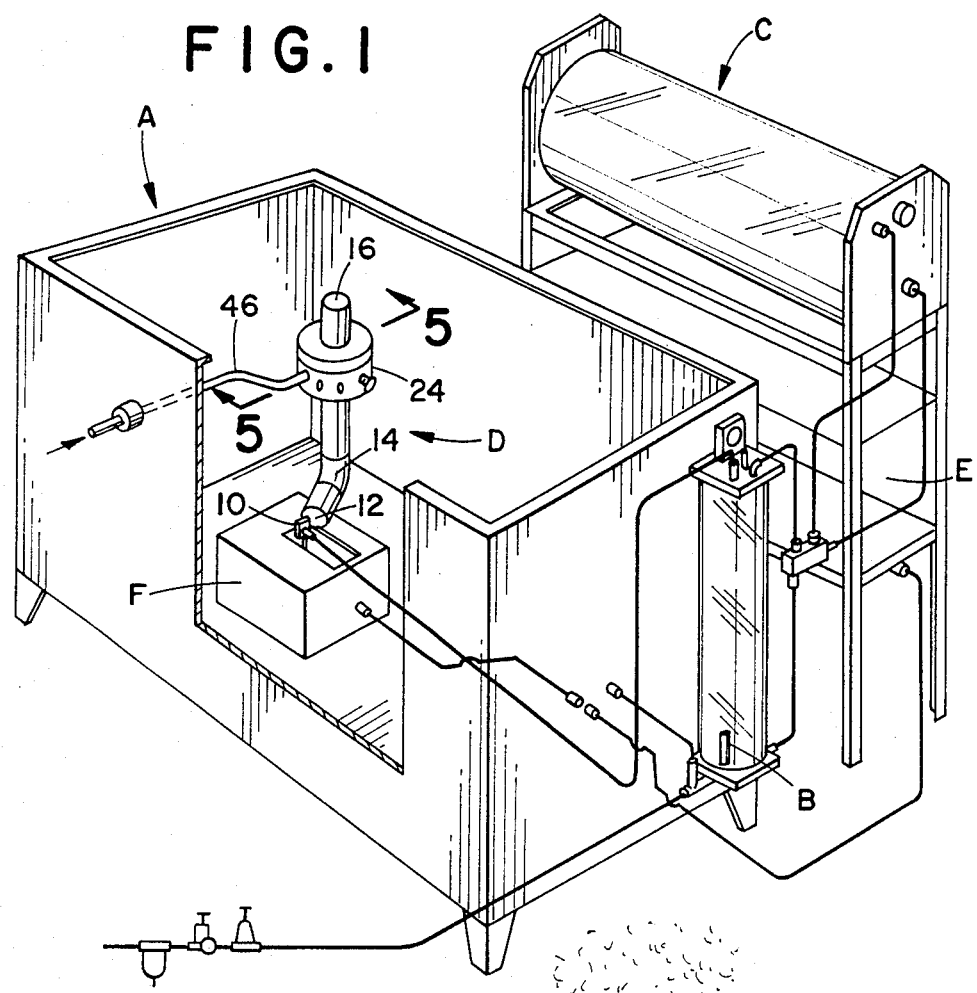

United States Patent [19]

Singleton et al.

[11] Patent Number: 4,752,446
[45] Date of Patent: Jun. 21, 1988

[54] CORROSION TEST CABINET CONTAMINANT MIXING APPARATUS

[75] Inventors: Raymund Singleton, 31653 Electric Blvd., Avon Lake, Ohio 44012; Norman B. Tipton, Avon Lake, Ohio

[73] Assignee: Raymund Singleton

[21] Appl. No.: 752,450

[22] Filed: Jul. 5, 1985

[51] Int. Cl.[4] .......................................... G01N 17/00
[52] U.S. Cl. ...................................... 422/53; 73/61.2; 366/107; 436/6
[58] Field of Search ............... 239/567, 424.5, 425, 239/426, 434; 137/561 A; 422/53; 261/18 R, 119 R; 73/61.2, 432.5 D; 366/107, 173

[56] References Cited

U.S. PATENT DOCUMENTS

| | | | |
|---|---|---|---|
| 648,263 | 4/1900 | Hull | 239/567 |
| 1,227,189 | 5/1917 | Ostrander | 239/567 |
| 1,329,649 | 2/1920 | Brombacher | 239/567 |
| 2,650,132 | 8/1953 | Reinecke | 239/567 |
| 3,019,090 | 1/1962 | Renshaw et al. | |
| 3,034,933 | 5/1963 | Richards | 134/28 |
| 3,273,802 | 9/1966 | Hull, Jr. | 73/432.5 D |
| 3,557,819 | 1/1971 | Singleton | 137/206 |
| 3,594,128 | 7/1971 | Singleton | 422/53 |
| 4,070,424 | 1/1978 | Olson et al. | 239/8 |
| 4,092,122 | 5/1978 | Suga | 422/53 |
| 4,114,813 | 9/1978 | Suga | 73/61.2 |
| 4,271,100 | 6/1981 | Trassy | 261/78 A |
| 4,289,732 | 9/1981 | Bauer et al. | 422/224 |
| 4,600,695 | 7/1986 | Cummings et al. | 422/53 |

Primary Examiner—Barry S. Richman
Assistant Examiner—Timothy M. McMahon
Attorney, Agent, or Firm—Fay, Sharpe, Beall, Fagan, Minnich & McKee

[57] ABSTRACT

A diffusing apparatus is adapted for vertically adjustable relation with a fog tower. A separate second corrosive fluid is emitted from plural outlets spaced approximately 45° apart along the exterior of the diffusing apparatus. The outlets direct the second corrosive fluid in a generally planar direction substantially perpendicular to the longitudinal axis of the fog tower for optimum uniform dispersion either alone or intermixing with a first corrosive fluid emitted from the fog tower.

9 Claims, 2 Drawing Sheets

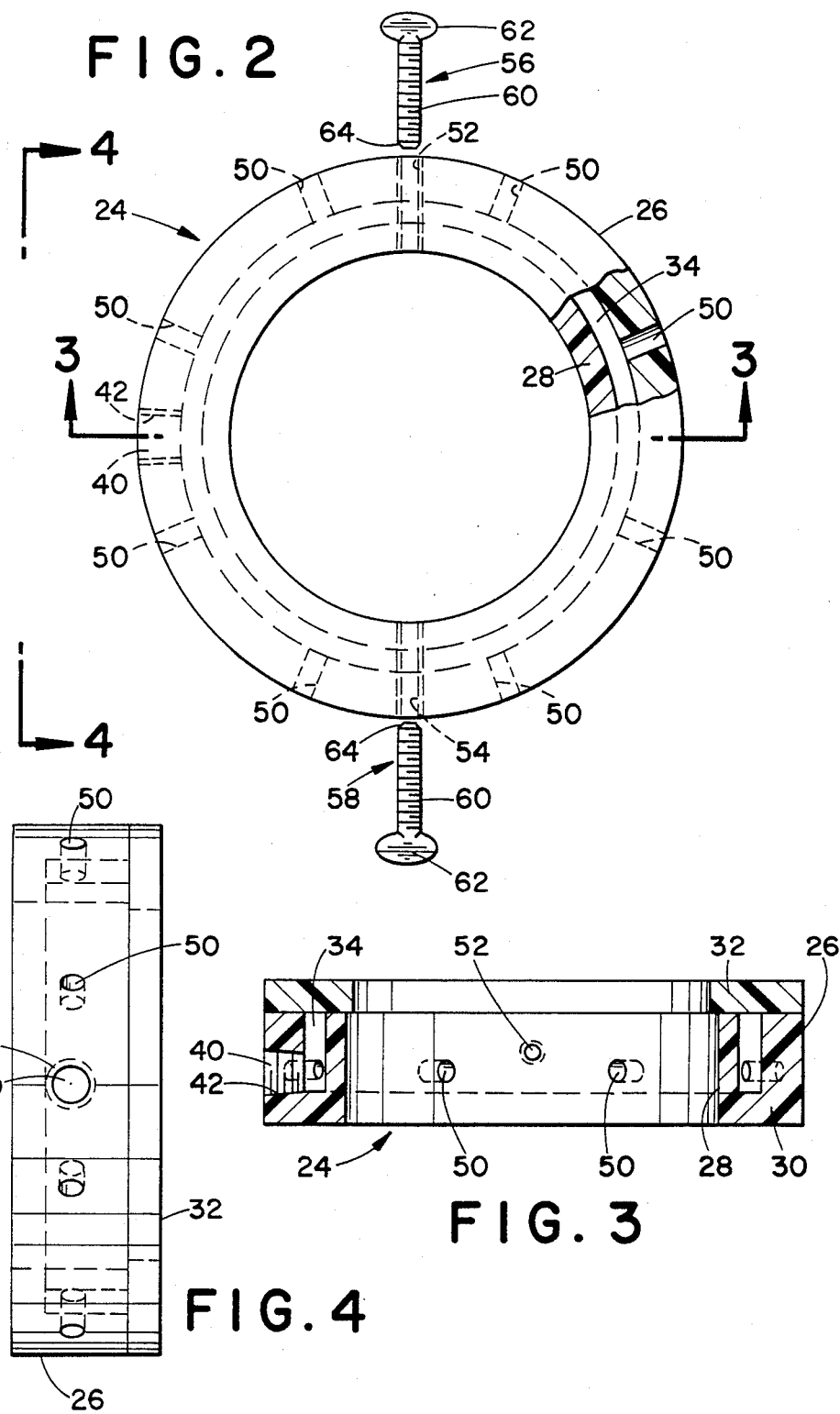

CORROSION TEST CABINET CONTAMINANT MIXING APPARATUS

BACKGROUND OF THE INVENTION

This invention pertains to the art of accelerated corrosion testing apparatus and more particularly to cabinet type testing apparatus. The invention is particularly applicable to a tubular corrosive fog generation tower and will be described with particular reference thereto although it will be appreciated that the invention has broader applications and may be advantageously employed in other environments and applications.

Industrial applications require stringent corrosion standards to be met before certain apparatus is marketed to the consumer public. Because of the nature of these standards, tests are conducted on a variety of specimens. One type of test is directed to the corrosion resistance of the specimen, which corrosion may be caused by excessive humidity, salt fog, corrosive gases, and the like. Conventionally, corrosion test cabinets, as described in U.S. Pat. Nos. 3,594,128 and 3,557,819, provide a controlled environment into which various specimens are introduced and subjected to extended corrosive action. The corrosion test cabinets must be capable of maintaining rigid standards and capable of repetition under identical conditions.

U.S. Pat. No. 3,594,128, which is hereby incorporated by reference, discloses a corrosion test cabinet having an angled tower portion whereby fluid flow from the nozzle is directed against an inner wall of the fog tower. Impingement of the fluid flow with the inner wall of the tower prevents the formation and emission of large droplets of corrosive fog and presents a more uniform fog environment in the test cabinet.

Prior art devices have failed to adequately intermix separate corrosive fluids. The combined effects of the separate corrosive fluids has herebefore been estimated through testing of the specimens in the separate corrosive environments and calculating the total corrosive effect on the specimens. Individual testing of the specimen for the separate corrosive fluids involves a great expenditure of time at an accordingly increased cost.

It has therefore been considered desirable to develop an improved corrosion test cabinet which provides simultaneous exposure of a specimen to separate corrosive fluids. Maintenance of the quality control standards as well as a uniform dispersion of the fluids throughout the cabinet are necessary design features incorporated into the subject new development.

SUMMARY OF THE INVENTION

According to the invention, a dispersion assembly utilized within a corrosion testing cabinet has a tower defining a fog conductive passageway along a first axis. A nozzle communicates with the tower at a tower inlet to thereby produce a first flow of corrosive fluid. A diffusing apparatus supplies a second corrosive fluid in a direction generally perpendicular to the first axis. The first and second corrosive fluids intermix within the test cabinet.

In accordance with another aspect of the invention, a means for adjustably attaching the diffusing apparatus to the tower is provided. Preferably, the adjustable attaching means includes a pair of diametrically opposed fastening members which operatively engage the diffusing apparatus to the tower.

In accordance with a further aspect of the invention, the diffusing apparatus is annularly shaped and constructed of a corrosion resistant material preferably, plastic.

In accordance with another aspect of the invention, the diffusing apparatus is provided with plural outlets and each outlet has a diameter typically in the range of 0.02 (0.05) to 0.25 (0.64) inches (cm).

A principle advantage of the present invention is the provision of a dispersion assembly readily adaptable to a corrosion testing cabinet.

Another advantage of the invention resides in the optimum uniform dispersion of a second fluid contaminant.

A further advantage of the invention is found in the adjustability of the diffusion apparatus with respect to the fog tower.

Still further advantages and benefits of the subject invention will become apparent to those skilled in the art upon a reading and understanding of the following detailed description.

BRIEF DESCRIPTION OF THE DRAWINGS

The invention may take physical form in certain parts and arrangements of parts. A preferred embodiment of which will be described in detail in this specification and illustrated in the accompanying drawings which form a part hereof, and wherein;

FIG. 1 is a perspective view of a corrosion testing cabinet;

FIG. 2 is a plan view of the diffusing apparatus;

FIG. 3 is a cross sectional view along the line 3—3 of FIG. 2;

FIG. 4 is a side view of the diffusing apparatus as seen along the line 4—4 of FIG. 2;

FIG. 5 is an enlarged cross sectional view of the tower and diffusing apparatus along the cut line 5—5 of FIG. 1.

DETAILED DESCRIPTION OF THE PREFERRED EMBODIMENT

Referring now to the drawings, the showings are for purposes of illustrating the preferred embodiment of the invention only and not for purposes of limiting same. FIG. 1 illustrates a corrosion test cabinet A which is utilized to subject various specimens to corrosive testing. A bubble tower B and associated reservoir C supply a humidified air to an opti-fog generator, which includes a fog tower D. A salt solution reservoir E feeds the opti-fog reservoir F with salt solution to be atomized as corrosive fog by the compressed, humdified air.

Briefly, the test cabinet interior is saturated with corrosive fluid by means of a nozzle 10 supplying a fine mist to an inlet 12 of the fog tower. A source of pressurized air (not shown) is combined with water and temporarily retained in the bubble tower B before transmission to the nozzle 10. Salt solution is drawn by venturi effect from reservoir F and atomized as corrosive fog by the pressurized, humdified air. The pressurized corrosive fluid exits the nozzle and impinges upon an elbow-shaped member 14 of the fog tower to prevent liquid or unatomized droplets from being emitted from the outlet 16 of the tower and into the test cabinet. The tower outlet is positioned near the top of the test cabinet interior and the fog is distributed axially upward and radially outward due to the continuous force of fog emitted by the nozzle. An exhaust fitting (not shown) is provided in the cabinet to maintain a constant test environment in the cabinet A. A clear plastic or similar material top (not shown) may be provided on the cabinet for visual monitoring of the specimen testing.

The nozzle is directed so that none of the corrosive spray can directly impinge on the test specimens placed within the cabinet A. Suitable racks (not shown) or other suspension means are provided for placement of the tested specimens at various predetermined locations within the test cabinet. Preferably, the racks are adjustable so that the specimens can be located at different lateral and axial positions varying in distance from the tower outlet. The test specimens are then subjected to a salt water fog, or another corrosive liquid or gas, for predetermined periods of time and at a constant environmental humidity. The corrosive fluid is automatically supplied to the fog tower and eliminates the necessity of constant monitoring of the tests. The test cabinets may also be equipped with recording instruments which monitor the relative humidity and/or temperature within the test cabinet. Further details of the structure and operation of a conventional corrosion test cabinet may be found in commonly assigned U.S. Pat. Nos. 3,557,819 and 3,594,128.

The subject new diffusing apparatus 24 is shown attached to the fog tower D in FIG. 1 forming a dispersion assembly. Details of the subject new development will be described with reference to FIGS. 2–5. A first or outer wall 26 of the diffusing apparatus is of generally circular configuration. The annularly shaped diffusing apparatus includes a second or inner wall 28 also of circular configuration and concentrically spaced with respect to the first wall 26. It will be appreciated that other design configurations may be used with equal success without departing from the scope and intent of the present invention. The second wall 28 is designed to have an inner diameter closely approximating the external diameter of the fog tower D so that it may be easily attached thereto as will be further explained hereinafter.

As seen in FIG. 3, the first and second walls may be cintegrally attached to a third or base wall 30 thus forming a cross sectional U-shaped member as seen in FIG. 3. Similarly, a fourth or top wall 32 may be welded or otherwise conventionally attached in sealing relation with the first and second walls 26, 28. A continuous curvilinear passage 34 is defined as extending radially between the first and second walls and axially extending between the third and fourth walls. As particularly seen in FIG. 2, the curvilinear passage 34 is annularly shaped and in concentrical relation with the first and second walls. Once again, the drawings are for mere illustration purposes alone, and other shapes and designs may be used with equal success. For example, the first, second, and third walls may be separately formed and attached in a conventional manner.

An inlet 40 extends through the first wall for operative communication with the curvilinear passage 34. The inlet includes a threaded interior 42 adapted to receive a mating end 44 of a connecting hose 46 which supplies a separate second corrosive fluid, for example $SO_2$, to the diffusing apparatus. Other corrosive fluids are also contemplated. Although illustrated with a single inlet, plural inlets may be used if desired. Plural outlets 50 also extend through the first wall 26 for operative communication with the curvilinear passage 34. The outlets are spaced approximatley 45° apart so that eight outlets are illustrated in FIG. 2. Of course, a different number of outlets may be incorporated into the diffusing apparatus design whereby the circumferential spacing of the outlets will vary accordingly. Preferably, the outlets are equally spaced along the exterior of the first wall 26 so that an even distribution of the second corrosive fluid may take place. The outlets are shown as bore holes ranging typically in size from 0.02 (0.05) to 0.25 (0.64) inches (cm) in diameter. The outlets are oriented generally perpendicular to the surface of the first wall 26 so that the second corrosive fluid is emitted from the outlets in a generally planar fashion. Other outlet orientations may be utilized, but the substantially planar emission from the diffusing apparatus achieves a uniform distribution and thorough intermixing of the first and second corrosive fluids.

A pair of threaded bore holes 52, 54 are provided at diametrically opposite positions of the diffusing apparatus 24 and adapted to receive a pair of fastening means 56, 58. The threaded fasteners 56, 58 provide a means for varying the axial attachment of the diffusing apparatus to the fog tower D. The variable axial attachment of the diffusing apparatus provides further control of the second corrosive fluid distribution and intermixing with the first corrosive fluid. The threaded fasteners may be of a variety of designs but as shown include a pair of conventional plastic or non-corroding thumb screws having an elongated threaded stem portion 60 and an enlarged flange head portion 62. The threaded bore holes 52, 54 are of a diameter closely associated with the stem portions 60, whereby the threaded fasteners 56, 58 are threadedly received therethrough so that an outer end 64 of the respective stem portions may engage the exterior wall of the fog tower D. Alternatively, the diffusing apparatus may be integrally formed with the fog tower which would, of course, eliminate the preferable axial adjustability of the diffusing apparatus.

It is desirable to construct the diffusing apparatus 24 of a corrosion resistant material since the internal passages as well as the external walls will be subjected to various corrosive fluids. Plastics may be used because of their ability to withstand corrosive effects as well as simple manufacture. Other corrosion resistant materials may be used with equal success.

Figure 5:
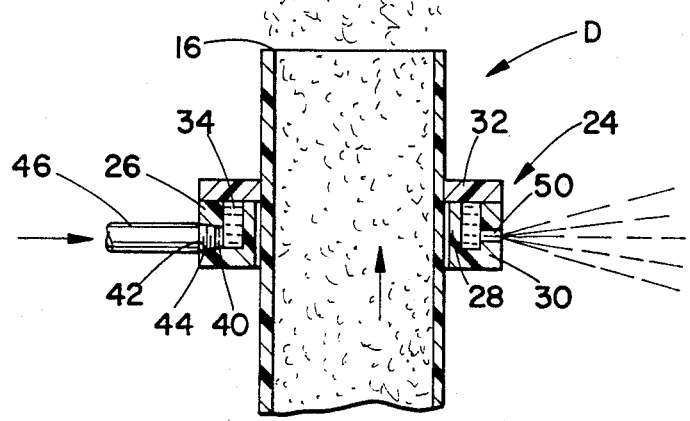

Reference to FIG. 5, particularly illustrates the interrelationship between the diffusing apparatus and the fog tower D. As briefly referred to above, a first corrosive fluid, commonly a salt water fog, passes through the elongated fog tower in a direction generally defined by the longitudinal axis of the fog tower. The first corrosive fluid is emitted from the tower outlet 16 whereby it disperses axially upward and radially outward for subsequent dispersion into the test cabinet interior. The subject new diffusing apparatus is axially positioned along the exterior of the fog tower for emission of a second corrosive fluid in a generally planar direction that is substantially perpendicular to the longitudinal axis of the fog tower. The connecting hose 46 communicates with a second corrosive fluid supply source and transmits the second fluid to the diffusing apparatus 24 and its associated inlet 40. The second corrosive fluid extends through the curvilinear passage 34 to the plural outlets 50 arranged along the exterior of the first wall 26. The second corrosive fluid is emitted in a substantially perpendicular relation with the first wall 26 into the test cabinet interior and intermixes with the first corrosive fluid. The spaced relation of the plural outlets 50 provides an optimum uniform dispersion of the second corrosive fluid into the cabinet interior. In this manner, a test specimen may be subject to plural corrosive fluids in a controlled environment.

Alternatively, the subject diffusing apparatus 24 may be used alone without subjecting the cabinet interior to plural contaminants. Various corrosive fluids may alternatively be connected by hose 46 for supplying a corrosive liquid or gas to the test cabinet. Greater versatility is achieved through provision of contaminants through the fog tower D and/or the diffusing appaaratus 24.

The invention has been described with reference to the preferred embodiment. Obviously, modifications and alterations will occur to others upon the reading and understanding of this specification. All such modifications and alterations are intended to be included in so far as they come within the scope of the appended claims or the equivalents thereof.

Having thus described the invention, what is claimed is:

1. A corrosion testing assembly comprising:
   a corrosion testing cabinet;
   a tower received in said cabinet and defining a fog conductive passageway therein;
   a nozzle communicating with said tower at a tower inlet positioned and arranged for producing a flow of a first corrosive fluid through a tower outlet to said cabinet generally along a first axis;
   a diffusing apparatus having plural diffusing outlets, said diffusing apparatus being received in said cabinet and positioned and arranged for supplying a second corrosive fluid thorugh the plural diffusing outlets to said cabinet generally along a plane substantially perpendicular to said first axis; and,
   means for adjusting the position of said diffusing apparatus in said cabinet along said first axis.

2. The corrosion testing assembly as defined in claim 1 wherein said adjusting means includes fastening means for operatively engaging said diffusing apparatus with said tower.

3. The corrosion testing assembly as defined in claim 1 wherein said diffusing apparatus is annularly shaped.

4. The corrosion testing assembly as defined in claim 1 wherein said plural outlets are spaced approximatley 45° apart.

5. The corrosion testing assembly as defined in claim 1 wherein said plural outlets are generally in the range of 0.02 to 0.25 inches in diameter.

6. The corrosion testing assembly as defined in claim 1 wherein said diffusing apparatus includes a continuous passageway formed between first and second generally circular walls.

7. The corrosion testing assembly as defined in claim 1 wherein said diffusing apparatus is constructed of corrosion resistant material.

8. The corrosion testing assembly as defined in claim 7 wherein said diffusing apparatus is constructed of plastic.

9. A corrosion testing assembly comprising:
   a corrosion testing cabinet;
   an elongated tubular tower received in said cabinet having an inlet end, an outlet end, and fog conductive passageway therebetween;
   a nozzle communicating with said tower inlet and positioned and arranged for producing a flow of first corrosive fluid to said cabinet along a first axis;
   a diffusing apparatus positioned and arranged for supplying a second corrosive fluid generally along a plane substantially perpendicular to said first axis;
   said diffusing apparatus being generally annularly shaped and defined by a pair of concentric first and second generally circular walls with a continuous passage defined therebetween;
   a diffusing apparatus inlet extending through said first wall and operatively connected to said continuous passage;
   a conducting tube positioned and arranged for interconnecting said diffusing apparatus inlet to an associated second corrosive fluid source;
   plural outlets operatively communicating with said continuous passage;
   means for adjustably attaching said diffusing apparatus to said tower whereby said diffusing apparatus may be variably positioned along said longitudinal axis; and,
   wherein said plural outlets are positioned and arranged for diffusing a second corrosive fluid to the cabinet.

* * * * *